United States Patent [19]

Johnson et al.

[11] Patent Number: 4,888,003
[45] Date of Patent: Dec. 19, 1989

[54] VACUUM APPARATUS

[76] Inventors: Gerald W. Johnson; Jeffrey W. Johnson, both of 821 Peakwood, Houston, Tex. 77090

[21] Appl. No.: 161,492

[22] Filed: Feb. 29, 1988

[51] Int. Cl.⁴ .............................................. A61M 1/00
[52] U.S. Cl. .................................. 604/319; 417/312; 604/119; 604/320
[58] Field of Search .............................. 604/118–120, 604/151–155, 317–321, 35; 417/38, 312, 313, 442

[56] References Cited

U.S. PATENT DOCUMENTS

| | | | |
|---|---|---|---|
| 3,191,600 | 6/1965 | Everett | 604/319 |
| 3,363,626 | 1/1968 | Bidwell et al. | 604/151 |
| 3,506,010 | 4/1970 | Murr | 604/151 |
| 3,723,027 | 3/1973 | Montelius | 417/313 |
| 3,799,702 | 3/1974 | Weishaar | 604/153 |
| 4,201,523 | 5/1980 | Olofsson | 417/313 |
| 4,264,282 | 4/1981 | Crago | 417/312 |
| 4,740,202 | 4/1988 | Stacey et al. | 604/320 |
| 4,747,761 | 5/1988 | Yumiyama et al. | 417/312 |

FOREIGN PATENT DOCUMENTS

| | | | |
|---|---|---|---|
| 3418341 | 11/1985 | Fed. Rep. of Germany | 604/319 |
| 0159786 | 7/1987 | Japan | 417/312 |

Primary Examiner—C. Fred Rosenbaum
Assistant Examiner—Mario Costantino
Attorney, Agent, or Firm—Neal J. Mosely

[57] ABSTRACT

A vacuum apparatus for surgical aspirators comprises a motor and vacuum pump on a supporting base with an evacuated chamber surrounding them to reduce noise produced by the apparatus. The apparatus preferably comprises first and second hollow housings of one or more wall members defining an enclosure surrounding the motor and pump, the wall members of said housings spaced apart to define a vacuum chamber around the motor and vacuum pump. The enclosure has an opening to surrounding atmosphere through the supporting base or through a sealed opening through the housings. The pump outlet communicates with surrounding atmosphere. A passageway connects the vacuum chamber both to the vacuum pump inlet and the exterior of the apparatus. Operation of said motor and pump is effective to withdraw air from the chamber to produce a vacuum therein supplied for use through the passageway, the vacuum is the reservoir being sufficient for use over a period of time and providing sound insulation against noise produced by the apparatus. The apparatus has pressure responsive valves for (1) preventing flow of air into the vacuum chamber when the surgical cannula is removed, (2) closing off the vacuum chamber from the surgical cannula when the vacuum is insufficient and causing the vacuum pump to work directly on the surgical cannula, and (3) shutting down the motor when the vacuum reaches a selected level.

24 Claims, 2 Drawing Sheets

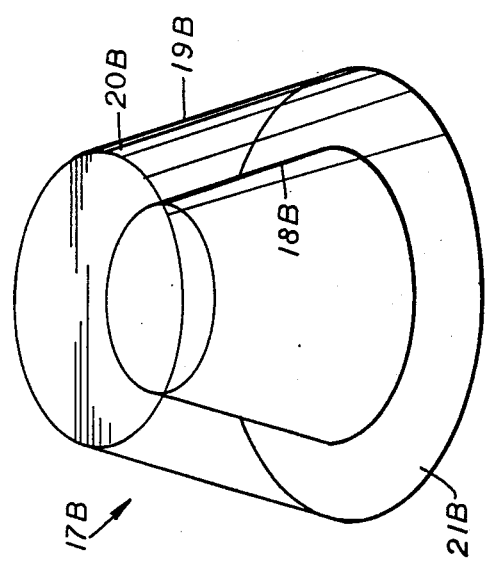
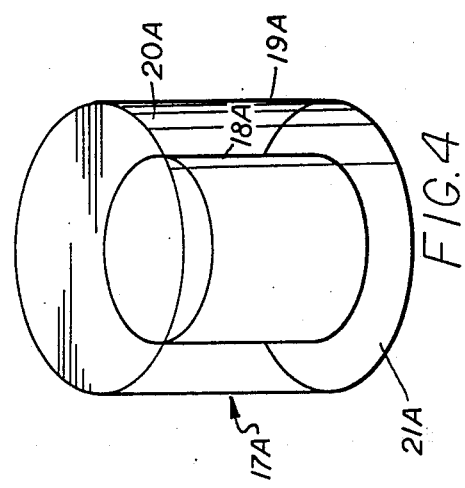
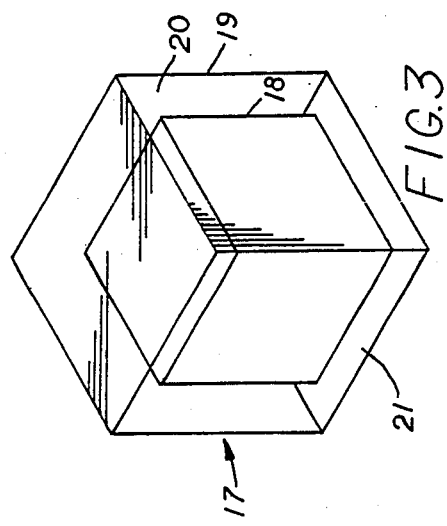
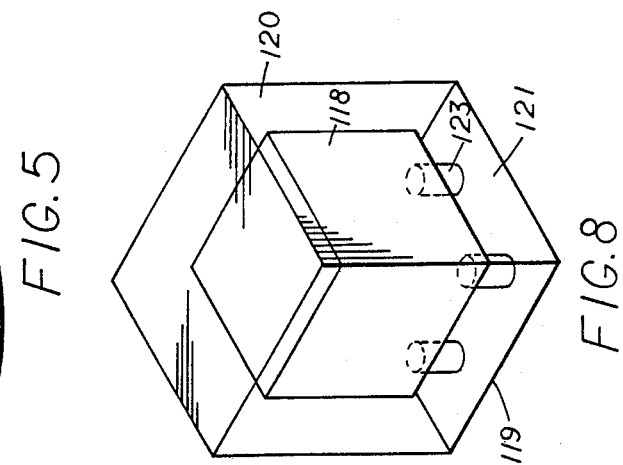
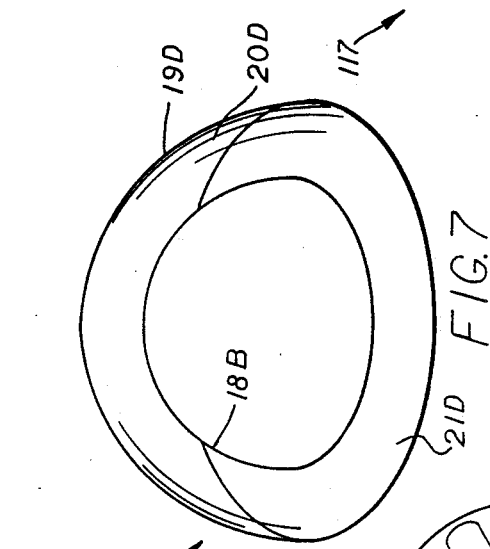
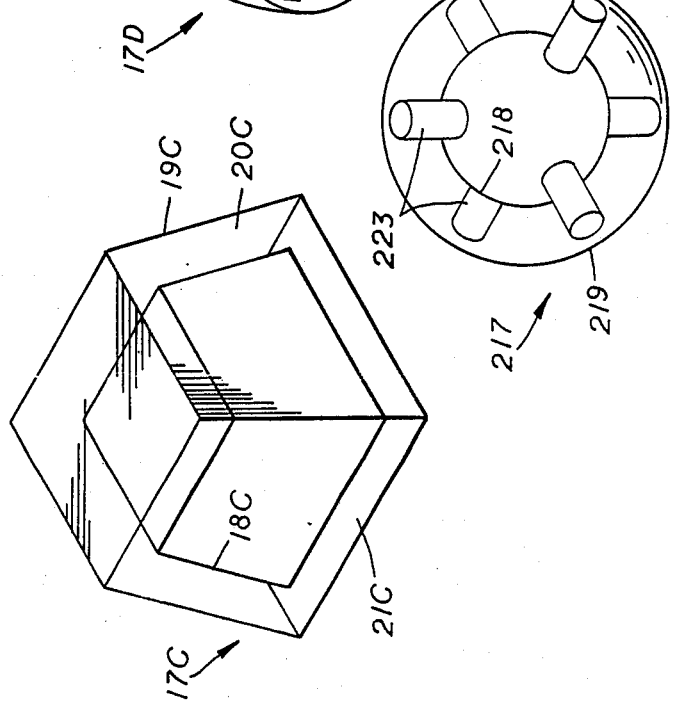

VACUUM APPARATUS

BACKGROUND OF THE INVENTION

1. Field of the Invention

This invention relates to new and useful improvements in vacuum apparatus for use in surgery and more particularly to vacuum apparatus having reduced output of noise and a reservoir sized to provide substantially instantaneous response when needed during surgery.

2. Brief Description of the Prior Art

Surgical aspirators presently available on the market were mostly adapted from vacuum extractors used by OB-GYN physicians for therapeutic abortions. These machines were slow to build up to maximum pressure, and generally had low volume flow rates at maximum vacuum. In order for vacuum to be available, the machines had to run continuously or be cut on and off, the surgeon having to wait several seconds for maximum vacuum to build up each time it is needed. Also, all of the early machines and most of the present-day machines are excessively noisy so that if the machine is being used for an hour or longer, the noise becomes an unpleasant factor.

Modern surgeons who use aspirators have a demand that the vacuum be continuously available for the entire surgical procedure. They want the machine to be able to deliver maximum vacuum as quickly as possible. The surgeon's cyclic need for maximum vacuum many times during the surgical procedure means that if there is a wait 5-10 second wait each time for the machine to reach maximum vacuum, the sum of all of the 5-10 second waiting periods can add up to a significant amount of time the patient is exposed to anesthesia.

Additionally, if the machine's flow rate at the maximum vacuum isn't high enough, the surgeon has to proceed with the surgery more slowly, again exposing the patient to longer periods of anesthesia.

The surgeon's need for the instant availability of maximum vacuum means the nurse or surgeon must manually cut the machine off and on, or the machine must run continuously, giving rise to noise pollution.

Most manufacturers of modern aspirators have tried to handle the surgeon's need for a high flow rate and rapid rise to maximum vacuum by placing two motors and two vacuum pumps into each machine and/or placing larger, more powerful motors and vacuum pumps in the aspirator.

A number of patents have dealt with the problems of noise abatement and reservoir size and utilization.

Guarniery U.S. Pat. No. 1,380,473 discloses a suction pump for player pianos having surrounding sound deadening material.

Vose U.S. Pat. No. 2,290,259 discloses a hair dryer with sound deadening material surrounding the fan motor.

Crago U.S. Pat. No. 4,264,282 discloses an air compressor pump having surrounding sound deadening material.

Wang et al. U.S. Pat. No. 4,395,258 discloses surgical vacuum apparatus with an accumulator and various control features.

Mayoral U.S. Pat. No. 4,676,779 discloses surgical vacuum apparatus with various control features.

Kayser U.S. Pat. No 4,315,506 discloses surgical vacuum apparatus for aspirating fluids from body cavities.

The prior art in general, and the cited patents in particular, does not disclose an apparatus with the control features provided by this invention or the complete sound deadening provided by utilizing the vacuum chamber as a sound insulator.

SUMMARY OF THE INVENTION

One of the objects of this invention is to provide a new and improved surgical vacuum apparatus having a vacuum accumulator with controls for improving the application of vacuum to the surgical site.

Another object of the invention is to provide a new and improved surgical vacuum apparatus having a vacuum accumulator with controls applying vacuum directly to the surgical site when the vacuum in the accumulator is insufficient.

Another object of the invention is to provide a new and improved surgical vacuum apparatus having a vacuum accumulator with controls shutting off the vacuum pump when the vacuum in the accumulator reaches a selected level.

Still another object of the invention is to provide a new and improved surgical vacuum apparatus having a vacuum accumulator with controls preventing air flow into the accumulator when the apparatus is shut down.

Still another object of the invention is to provide a new and improved surgical vacuum apparatus having a vacuum accumulator which surrounds the motor and vacuum pump to provide sound insulation.

Other objects of the invention will become apparent from time to time throughout the specification and claims as hereinafter related.

The foregoing objects and other objects of the invention are accomplished by a vacuum apparatus for surgical aspirators which comprises a motor and vacuum pump on a supporting base with an evacuated chamber surrounding them to reduce noise produced by the apparatus.

The apparatus preferably comprises first and second hollow housings of one or more wall members defining an enclosure surrounding the motor and pump, the wall members of said housings spaced apart to define a vacuum chamber around the motor and vacuum pump.

The enclosure has an opening to surrounding atmosphere through the supporting base or through a sealed opening through the housings. The pump outlet communicates with surrounding atmosphere. A passageway connects the vacuum chamber both to the vacuum pump inlet and the exterior of the apparatus.

Operation of said motor and pump is effective to withdraw air from the chamber to produce a vacuum therein supplied for use through the passageway, the vacuum in the reservoir being sufficient for use over a period of time and providing sound insulation against noise produced by the apparatus.

The apparatus has pressure responsive valves for (1) preventing flow of air into the vacuum chamber when the surgical cannula is removed, (2) closing off the vacuum chamber from the surgical cannula when the vacuum is insufficient and causing the vacuum pump to work directly on the surgical cannula, and (3) shutting down the motor when the vacuum reaches a selected level.

BRIEF DESCRIPTION OF THE DRAWINGS

FIG. 3 is an isometric view of the accumulator or reservoir chamber for the apparatus shown in FIG. 1.

FIG. 4 is an isometric view of a different configuration, i.e., cylindrical, for the accumulator or reservoir chamber for the apparatus shown in FIG. 1.

FIG. 5 is an isometric view of a different configuration, i.e., frusto-conical, for the accumulator or reservoir chamber for the apparatus shown in FIG. 1.

FIG. 6 is an isometric view of a different configuration, i.e., frusto-pyramidal, for the accumulator or reservoir chamber for the apparatus shown in FIG. 1.

FIG. 7 is an isometric view of a different configuration, i.e., hemispherical, for the accumulator or reservoir chamber for the apparatus shown in FIG. 1.

FIG. 8 is an isometric view of a different configuration for the accumulator or reservoir chamber for the apparatus shown in FIG. 1 in which a cubic chamber completely surrounds the vacuum pump and motor.

FIG. 9 is an isometric view of a different configuration for the accumulator or reservoir chamber for the apparatus shown in FIG. 1 in which a spherical chamber completely surrounds the vacuum pump and motor.

DESCRIPTION OF THE PREFERRED EMBODIMENTS

Figure 1:
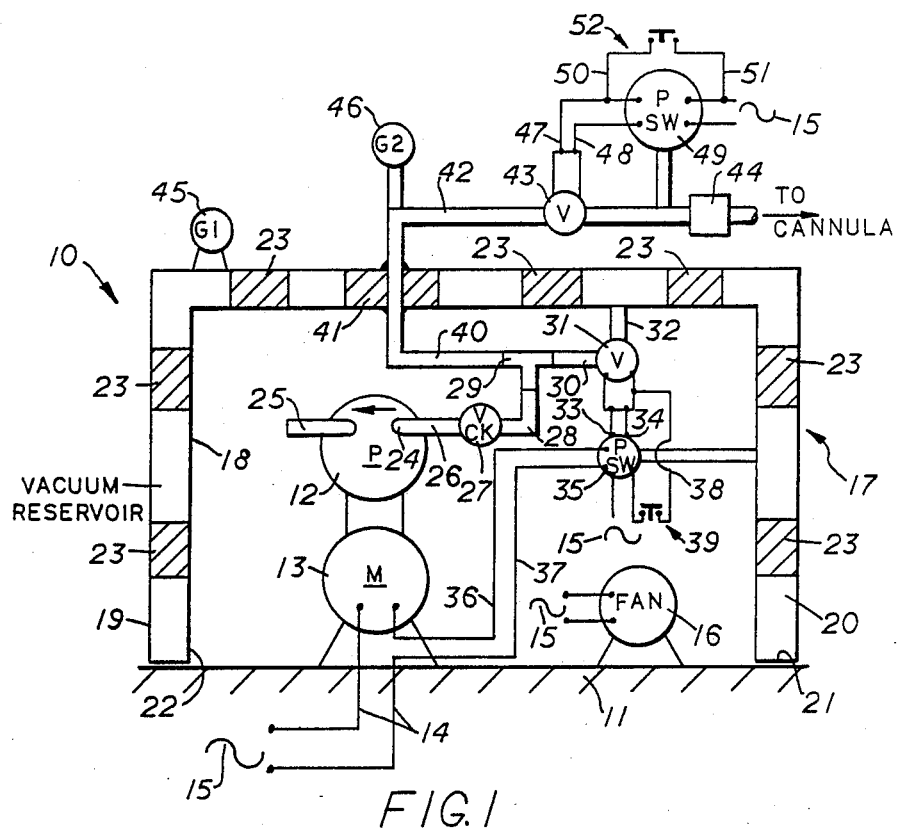
FIG. 1 is a schematic view of a surgical vacuum apparatus illustrating a preferred embodiment of the invention.
Figure 2:
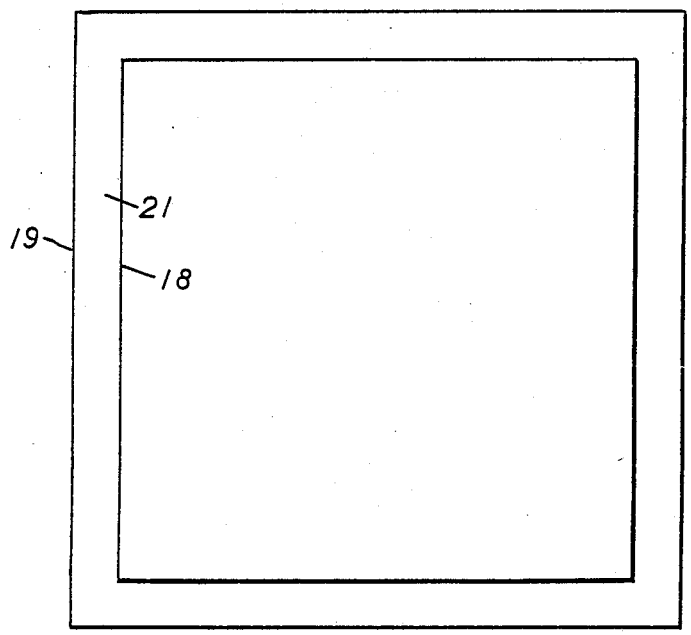
FIG. 2 is bottom view of the vacuum reservoir or accumulator for the apparatus shown in FIG. 1.

Referring to the drawings by numerals of reference, there is shown in FIG. 1 a surgical vacuum apparatus 10 illustrating a preferred embodiment of the invention.

Vacuum apparatus 10 has a supporting base 11 on which there are supported a vacuum pump 12 and motor 13 for driving the vacuum pump. Motor 13 is connected to electric leads 14 to a power source 15. A fan 16 is positioned to circulate air for cooling vacuum pump 12 and motor 13.

A vacuum accumulator or reservoir 17 covers vacuum pump 12, motor 13 and fan 16 to provide sound insulation for the apparatus as described below. Reservoir 17 comprises an inner housing 18 and outer housing 19 of cubic construction. The space between housings 18 and 19 defines a reservoir chamber 20 closed and sealed by a bottom wall 21. Reservoir 17 is hollow, i.e. forms an enclosure, with a bottom opening 22 allowing it to be fitted over the base 11 enclosing the vacuum pump 12, motor and fan 16 on all sides.

Reservoir 17 preferably has a plurality of spacer members 23 between the housings 18 and 19 to support the walls thereof against collapse when reservoir chamber 20 is evacuated. If the walls of housings 18 and 19 are sufficiently strong, spacer members 23 may be eliminated.

The pump 12 has an inlet 24 connected to vacuum reservoir chamber and an outlet 25 open to the space or enclosure surrounding vacuum pump 12 and motor 13 and communicating with surrounding atmosphere. In the embodiments, viz., FIGS. 1-7, where the bottom of reservoir 17 is open, as at 22, air discharged by vacuum pump 12 leaks to atmosphere through the bottom opening. In embodiments, such as FIGS. 8 and 9, where the vacuum pump and motor are completely enclosed, the pump outlet in connected to a conduit (not shown) extending through and sealed in the walls of the inner and outer housings to discharge to atmosphere.

Pump inlet 24 is connected by conduit 26 to one side of a check valve 27, the other side of which is connected by conduit 28 to the stem of a tee 29. One side of tee 29 is connected to the outlet 30 from a solenoid valve 31 which has its inlet connected by conduit 32 opening into vacuum reservoir chamber 20.

Solenoid valve has its coil connected by electric leads to connections 33 and 34 on a pressure regulating switch 35. Leads 36 and 37 connect switch 35 in circuit with motor leads 14. An electric lead 38 bypasses switch 35 and is connected to normally closed switch 39 which is opened by manual or pedal action.

Pressure regulating switch 35 may be a double switch, or a group of switches, which is connected to respond to pressure in vacuum chamber 20 and has contacts controlling motor 13 and solenoid valve 31. Pressure responsive means for operating the switch contacts may be of any conventional type, including bellows, diaphragm, Bourdon tube, etc., and is settable to operate at a selected pressure. The pressure responsive means may operate against a spring having an operator to vary the spring force and thus select the pressure of operation of the switch. One set of switch contacts are operated at a pressure selected by the operator to shut off motor 13 at a selected low pressure (high vacuum). Another set of switch contacts are operated at a pressure selected by the operator to close the normally open solenoid valve 31 at a selected higher pressure (low vacuum).

The other side of tee 29 is connected by conduit to a sealed connection 41 through vacuum chamber 20. Sealed connection 41 may be made through a hole in one of the spacer members 23 or a section of the conduit may be sealed in the walls of housings 18 and 19. Sealed connection 41 is connected by conduit 42 to one side of a solenoid valve 43, the other side of which is connected to a receptacle 44 for the conduit or tubing from a surgical cannula (not shown). Gauges 45 and 46 are positioned to register the pressure (vacuum) in vacuum chamber 20 and in line 42 to the surgical cannula, respectively. Solenoid valve 43 has electrical connections 47 and 48 to one side of a pressure regulating switch 49, the other side of which is connected to the power source. Leads 50 and 51 are connected to a normally open, manual or pedal switch 52 which bypasses pressure regulating switch 49.

Pressure regulating switch 49 may be a single switch, or a group of switches, which is connected to respond to pressure in vacuum line 42 leading to the surgical cannula and has contacts controlling solenoid valve 43. Pressure responsive means for operating the switch contacts may be of any conventional type, including bellows, diaphragm, Bourdon tube, etc., and is settable to operate at a selected pressure. The pressure responsive means may operate against a spring having an operator to vary the spring force and thus select the pressure of operation of the switch. The switch contacts are operated at a pressure selected by the operator to close the open solenoid valve 43 in response to higher pressure (atmospheric pressure) encountered at the receptacle 44 for the surgical cannula when the cannula is removed at the end of surgery.

Reservoir 17 may be of any suitable shape so long as it is hollow to fit over the base 11 enclosing the vacuum pump 12, motor and fan 16 on all sides. A variety of shapes are shown in the isometric views shown in FIGS. 3-7. In these embodiments, there is essentially no change in the location of the pump 12 and motor 13 and the connections thereto, since the only change is in the shape of the housings providing the vacuum chamber 20 surrounding the pump and motor.

In FIG. 3, reservoir 17 is formed by a housing 18 of cubic shape within a housing 19 of cubic shape with end wall 21 closing the reservoir chamber 20. In FIG. 4, reservoir 17a is formed by a housing 18a of cylindrical shape within a housing 19a of cylindrical shape with end wall 21a closing the reservoir chamber 20a.

In FIG. 5, reservoir 17b is formed by a housing 18b shape with end wall 21b closing the reservoir chamber of frusto-conical shape within a housing 19b of frusto-conical 20b. In FIG. 6, reservoir 17c is formed by a housing 18c having the shape of a truncated pyramid within a housing 19c of like Shape with end wall 21c closing the reservoir chamber 20c. In FIG. 7, reservoir 17d is formed by a housing 18d of hemispherical shape within a housing 19d of hemispherical shape with end wall 21d closing the reservoir chamber 20d.

Alternate embodiments of the vacuum reservoir for the apparatus are shown in FIGS. 8 and 9. The embodiment shown in FIG. 8 comprises a vacuum reservoir 117 formed by inner housing 118, which is a completely closed cube, positioned inside outer housing 119, which is a completely closed cube. The bottom wall of housing 118 is spaced from and supported on the bottom wall 121 of outer housing 119 by spacer members 123 so that the vacuum reservoir chamber 120 surrounds the motor and pump on all sides and top and bottom. In this embodiment, the bottom wall of inner housing 118 performs the function of supporting base 11 in supporting the vacuum pump and motor.

The embodiment shown in FIG. 9 comprises a vacuum reservoir 217 formed by inner, closed, spherical housing 218 positioned inside outer, closed, spherical housing 219. The wall of spherical housing 218 is spaced from and supported on the wall of outer spherical housing 219 by spacer members 223 so that the vacuum reservoir chamber 220 surrounds the motor and pump on all sides and top and bottom. In this embodiment, the bottom wall portion of inner spherical housing 118 performs the function of supporting base 11 in supporting the vacuum pump and motor.

In the embodiments of FIGS. 8 and 9, there are minor, obvious changes required in the location of the pump 12 and motor 13 and the connections thereto, since the housings providing the vacuum chamber 120 or 220 surround the pump and motor on all sides, including top and bottom. Consequently, all connections which were made through the open bottom of vacuum reservoir 17 or through or along supporting base 11, must be made through sealed openings in the outer and inner housings which form the vacuum reservoir.

OPERATION

The operation of the apparatus should be fairly apparent from the structural description, above, but will be described below in more detail. As previously noted, the use of a vacuum reservoir chamber shaped to enclose the motor and vacuum pump provides a highly efficient sound insulation for the apparatus. The controls provide for a variety of manually controlled and automatically controlled features of operation. Thus, the reservoir is a vacuum accumulator which provides a source of vacuum sufficient for about one or two minutes, depending on size.

In one prototype, reservoir 20 was a 2" thick chamber around the inner wall that covered the motors, pumps and ventilating fans, a space of about 1.25 cu.ft. Since most aspirators will pump between 0.3 and 0.7 cu.ft. or air per minute at 27" of mercury vacuum, the apparatus provides over 60 seconds head-start compared to other aspirators. Additionally, since the vacuum chamber is the 2" thick area on all sides of the motor chamber (except the bottom), and since no sound is transmitted through a vacuum, excellent sound-insulation is provided.

On start-up of the apparatus, solenoid valve 31 is open connecting vacuum pump 12 to vacuum chamber 20. The vacuum reservoir is likely to be at atmospheric pressure unless there is some residual vacuum from a previous operation. Solenoid valve 43 is closed preventing application of vacuum at the surgical cannula receptor 44. When the vacuum pump 12 is started up, air is drawn from vacuum reservoir chamber 20 and the vacuum line up to solenoid valve 43.

After an appreciable draw-down of pressure in reservoir chamber 20, the operator sets pressure regulating switch 35 to a selected high vacuum (low pressure) for the contacts controling pump motor 13, and a selected lower vacuum (higher pressure) for the contacts controling solenoid valve 31.

After the vacuum is drawn down to the point where pressure regulator switch shuts down motor 13, the operator (surgeon or his assistant) connects the surgical cannula to receptor 44. Since solenoid valve 43 is closed, it is necessary to operate manual or pedal switch 52 to bypass pressure regulator switch 49. This opens valve 43 to allow vacuum to draw air from the surgical cannula to keep the surgical site clear. At this point, the vacuum in line 42 is exposed to pressure regulator switch to open solenoid valve 43 and hold it open during continued operation.

As the pressure drops in vacuum chamber 20, pressure regulator switch first closes the contacts starting motor 13 and then closes the contacts controling solenoid valve 30 to close it and cause vacuum pump 12 to work directly on drawing air (creating vacuum) from lines 40 and 42 leading to the surgical cannula.

When the operation is completed, the surgeon (or his assistant) removes the cannula from connector 44. Air, at atmospheric pressure, then enters line 42. This pressure acts on pressure regulator switch 49 to close solenoid valve 43 to prevent air from entering the apparatus and destroying the vacuum. In this condition, check valve 27 prevents air from entering the vacuum chamber 20 through pump 12.

The arrangement of valves and control switches used herein allows the pump to run less than 50% (and possibly less than 25%) of the time its is required to run if there is no vacuum reservoir or electronic controls, thus diminishing the amount of noise pollution. The vacuum in chamber 20 surrounding the motor, pump and fan further reduces the amount of noise.

While this invention has been described fully and completely, with special emphasis on the preferred embodiments, it should be understood that, within the scope of the appended claims, the invention may be practiced otherwise than as specifically described herein.

We claim:
1. A vacuum apparatus for surgical aspirators comprising:

a first hollow housing comprising one or more wall members defining an enclosure, a second hollow housing comprising one or more wall members surrounding and spaced from said first hollow housing and defining a chamber therebetween, means sealing said chamber to provide a vacuum reservoir, said enclosure having an opening to surrounding atmosphere, a supporting base in said enclosure, a vacuum pump positioned on said base in said enclosure and having an inlet and outlet, a motor positioned on said base in said enclosure and connected to and operable to drive said pump, power means for operating said motor, means connecting said pump inlet to said vacuum chamber, said pump outlet being open to said enclosure and communicating with surrounding atmosphere, a passageway connecting said chamber to the exterior of said apparatus, and operation of said motor and pump by said power means being effective to withdraw air from said chamber to produce a vacuum therein supplied for use through said passageway, the vacuum in said reservoir being sufficient for use over a period of time and providing sound insulation against noise produced by the apparatus.

2. A vacuum apparatus for surgical aspirators according to claim 1 including
spacer members positioned between said first housing and said second housing wall members in supporting relation thereto to prevent collapse when said chamber is evacuated.

3. A vacuum apparatus for surgical aspirators according to claim 1 in which
said first and said second housings have a common base wall forming said chamber sealing means and resting on said supporting base.

4. A vacuum apparatus for surgical aspirators according to claim 1 in which
said first and said second housings have a common base wall, forming said chamber sealing means, resting on said supporting base and open at the bottom to fit removably over said motor and pump on said supporting base.

5. A vacuum apparatus for surgical aspirators according to claim 1 in which
said first housing completely surrounds said enclosure and is surrounded on all sides by said second housing so that said chamber completely surrounds said enclosure and the motor and pump supported therein, one wall of said first housing comprising said supporting base.

6. A vacuum apparatus for surgical aspirators according to claim 1 in which
said first and said second housings have a common base wall, forming said chamber sealing means, resting on said supporting base and open at the bottom to fit removably over said motor and pump on said supporting base, and further includes
spacer members positioned between said first housing wall and said second housing wall in supporting relation thereto to prevent collapse when said chamber is evacuated.

7. A vacuum apparatus for surgical aspirators according to claim 1 in which
said first housing completely surrounds said enclosure and is surrounded on all sides by said second housing so that said chamber completely surrounds said enclosure and the motor and pump supported therein, one wall of said first housing comprising said supporting base, and further includes
spacer members positioned between said first housing wall and said second housing wall in supporting relation thereto to prevent collapse when said chamber is evacuated.

8. A vacuum apparatus for surgical aspirators according to claim 1 in which
said first and said second housings have a common base wall and a plurality of planar walls and said chamber surrounds said first housing except for the base thereof.

9. A vacuum apparatus for surgical aspirators according to claim 1 in which
said first and said second housings have a common base wall and curved walls and said chamber surrounds said first housing except for the base thereof.

10. A vacuum apparatus for surgical aspirators according to claim 1 in which
said first and said second housings each have at least one curved wall,
said first sealed housing is surrounded on all sides by said second sealed housing and said chamber surrounds said first housing on all sides.

11. A vacuum apparatus for surgical aspirators according to claim 1 in which
said first and said second housings have a common base wall and a plurality of planar walls and said chamber surrounds said first housing except for the base thereof, and further includes
spacer members positioned between said first housing wall and said second housing wall in supporting relation thereto to prevent collapse when said chamber is evacuated.

12. A vacuum apparatus for surgical aspirators according to claim 1 in which
said first and said second housings have a plurality of planar walls,
said first sealed housing is surrounded on all sides by said second sealed housing and said chamber surrounds said first housing on all sides, and further includes
spacer members positioned between said first housing wall and said second housing wall in supporting relation thereto to prevent collapse when said chamber is evacuated.

13. A vacuum apparatus for surgical aspirators according to claim 1 in which
said first and said second sealed housings have a common base wall and curved walls and said chamber surrounds said first housing except for the base thereof, and further includes
spacer members positioned between said first housing wall and said second housing wall in supporting relation thereto to prevent collapse when said chamber is evacuated.

14. A vacuum apparatus for surgical aspirators according to claim 1 in which
said first and said second sealed housings each have at least one curved wall,
said first sealed housing is surrounded on all sides by said second sealed housing and said chamber surrounds said first housing on all sides, and further includes spacer members positioned between said first housing wall and said second housing wall in supporting relation thereto to prevent collapse when said chamber is evacuated.

15. A vacuum apparatus for surgical aspirators according to claim 1 including spacer members positioned between said first housing wall and said second housing wall in supporting relation thereto to prevent collapse when said chamber is evacuated, and said passageway from said first sealed housing communicating with the exterior of said apparatus comprising a passageway through said first housing wall, one of said spacer members, and said second housing wall.

16. A vacuum apparatus for surgical aspirators according to claim 1 including conduit means connecting the inlet of said pump to the exterior of said apparatus and to said chamber.

17. A vacuum apparatus for surgical aspirators according to claim 1 including spacer members positioned between said first housing wall and said second housing wall in supporting relation thereto to prevent collapse on evacuation, conduit means connecting the inlet of said pump to the exterior of said apparatus through one of said spacer members and to said chamber.

18. A vacuum apparatus for surgical aspirators according to claim 1 including a check valve, connected between said chamber and the inlet to said pump, which permits movement of air only from said chamber to said pump.

19. A vacuum apparatus for surgical aspirators according to claim 1 including a conduit connecting said chamber to the exterior of the apparatus for connection to a surgical cannula, solenoid valve means operable to control application of vacuum to a surgical cannula, pressure responsive means operable to control operation of said solenoid valve means to apply vacuum directly from said pump to the surgical cannula on occurrence of a predetermined pressure in said chamber.

20. A vacuum apparatus for surgical aspirators according to claim 19 including solenoid valve means on said apparatus at the point of connection of the surgical cannula, and pressure responsive means operable to sense change of pressure which occurs when the cannula is removed from the patient to close said last named solenoid valve, thereby preventing the vacuum in said chamber from being depleted.

21. A vacuum apparatus for surgical aspirators according to claim 19 including solenoid valve means on said apparatus at the point of connection of the surgical cannula, first pressure responsive means operable to sense change of pressure which occurs when the cannula is removed from the patient to close said last named solenoid valve, thereby preventing the vacuum in said chamber from being depleted, and second pressure responsive means operable to deenergize said motor and pump on occurrence of a selected low pressure in said chamber when no vacuum is being used by the apparatus.

22. A vacuum apparatus for surgical aspirators comprising:

a vacuum pump having an inlet and outlet, a motor connected to and operable to drive said pump, power means for operating said motor, a vacuum accumulator chamber, means connecting said pump inlet to said vacuum chamber, said pump outlet being open to atmosphere, conduit means connecting said chamber to an exterior connector for connection to a surgical cannula, first solenoid valve means connected to selectively connect said vacuum chamber or the inlet from said pump to said conduit means to control application of vacuum through said conduit means to a surgical cannula, first pressure responsive means connected to control operation of said first solenoid valve means to apply vacuum directly from said pump to the surgical cannula on occurrence of a predetermined pressure in said vacuum chamber, second solenoid valve means on said apparatus at the point of connection of the surgical cannula, and second pressure responsive means positioned to sense change of pressure which occurs when the cannula is removed from the patient to close said second solenoid valve means, thereby preventing the vacuum in said chamber from being depleted, and operation of said motor and pump by said power means being effective to withdraw air from said chamber to produce a vacuum therein supplied for use through said passageway, the vacuum in said reservoir being sufficient for use over a period of time.

23. A vacuum apparatus for surgical aspirators according to claim 22 further including a check valve, connected between said chamber and the inlet to said pump permitting movement of air only from said chamber to said pump.

24. A vacuum apparatus for surgical aspirators according to claim 22 in which said first pressure responsive means includes means to deenergize said motor and pump on occurrence of a selected low pressure in said chamber when no vacuum is being used by the apparatus.

* * * * *